United States Patent [19]

Matthews et al.

[11] Patent Number: 5,147,863

[45] Date of Patent: Sep. 15, 1992

[54] 2,2'-BI-1H-IMIDAZOLES

[75] Inventors: Donald P. Matthews, West Chester; Jeffrey P. Whitten, Cincinnati; James R. McCarthy, West Chester, all of Ohio

[73] Assignee: Merrell Dow Pharmaceuticals Inc., Cincinnati, Ohio

[21] Appl. No.: 600,295

[22] Filed: Oct. 17, 1990

Related U.S. Application Data

[63] Continuation of Ser. No. 213,552, Jun. 30, 1988, abandoned, which is a continuation-in-part of Ser. No. 922,331, Oct. 30, 1986, abandoned, and Ser. No. 801,458, Nov. 25, 1985, abandoned.

[51] Int. Cl.$^5$ .................. A61K 31/695; A61K 31/44; A61K 31/415; C07D 403/00
[52] U.S. Cl. ..................... 514/63; 548/336; 546/278; 514/341; 514/397
[58] Field of Search .............. 548/336; 546/278; 514/341, 397, 63

[56] References Cited

U.S. PATENT DOCUMENTS

| | | | |
|---|---|---|---|
| 2,155,555 | 4/1939 | Karrer | 548/336 |
| 4,347,364 | 8/1982 | Walser et al. | 546/256 |
| 4,466,976 | 8/1984 | Klose et al. | 546/256 |

FOREIGN PATENT DOCUMENTS 2149825  4/1972  Fed. Rep. of Germany ...... 548/336

OTHER PUBLICATIONS

Chem. Abs., vol. 80, 80:82801a (1974).
K. Lehmstedt et al., Chemische Berichte, 76(B), 879–891 (1943).
P. Melloni et al., J. Med. Chem., 15(9), 926–930 (1972).
P. Rasmussen et al., J. Am. Chem. Soc., 104, 6155-156 (1982).
Chemical Abstracts 93:187324u (1980).

Primary Examiner—Mary C. Lee
Assistant Examiner—Robert C. Whittenbaugh
Attorney, Agent, or Firm—John J. Kolano

[57] ABSTRACT

This invention relates to novel derivatives of 2,2'-bi-1H-imidazoles, to the processes and intermediates used in their preparation, to their ability to exert the pharmacologic effects of lowering high blood pressure and of increasing heart contractile force and to their use as chemotherpauetic agents useful in treating cardiac insufficiency and hypertension.

14 Claims, No Drawings

2,2'-BI-1H-IMIDAZOLES

This is a continuation of application Ser. No. 07/213,552 filed Jun. 30, 1988, (now abandoned), which is a continuation-in-part of application Ser. No. 06/922,331, filed Oct. 30, 1986 (now abandoned), and a continuation-in-part of application Ser. No. 06/801,458, filed Nov. 25, 1985 (now abandoned).

This invention relates to 2,2'-bi-1H-imidazoles and to the processes for their preparation and their use as chemotherapeutic agents.

More specifically, this invention relates to novel derivatives of 2,2'-bi-1H-imidazoles, to the processes and intermediates used in their preparation, to their ability to exert the pharmacologic effects of lowering high blood pressure and of increasing heart contractile force and to their use as chemotherapeutic agents useful in treating cardiac insufficiency and hypertension.

Still more specifically, this invention relates to 2,2'-bi-1H-imidazoles of the formula

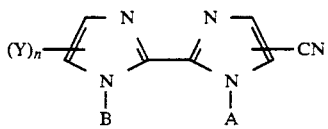

and the tautomers thereof, and the pharmaceutically acceptable salts thereof wherein $Y_n$ is hydrogen, halogen, cyano, $C_{1-6}$ alkyl, $C_{1-6}$ alkoxy, $CF_3$, 2-, 3-, or 4-pyridyl, $COOR^1$, $CONH_2$, —S(O)$_m$R, phenyl and R-substituted phenyl; with R being hydrogen, $C_{1-6}$ alkyl, halogeno, nitro, amino, $C_{1-6}$ alkoxy, $CF_3$, or —S(O)$_m$R$^2$; R$^1$ is hydrogen or $C_{1-6}$ alkyl; R$^2$ is $C_{1-6}$ alkyl; m is 0, 1 Or 2 and n is 1 or 2;

A is hydrogen or $C_{1-6}$ alkyl;

B is hydrogen or methyl, ethyl, vinyl, phenyl or benzyl with the proviso that at least one of A or B is hydrogen.

It is to be noted that when A or B is other then hydrogen, then tautomerism can not take place in the imidazole ring involved and the 4- or 5-positions (or the 4'- or 5'-positions) are fixed and different. The —CN and/or Y-substituent can then be located at either of these positions with respect to each imidazole ring. On the other hand, when A and/or B is hydrogen, then tautomerism can take place and the hydrogen could actually be located on either nitrogen in an imidazole ring. In that case, although the structure may be assigned with the —CN and/or Y-substituent at the 4- or 4'-position, tautomerism can take place and the same substituents would be considered as located at the 5- or 5'-position in the other tautomeric form. Thus, in that type of tautomeric situation, the position of any substituent is ordinarily designated as 4(5)- or 4'(5')-, respectively. That is, in such a situation, the 4- and 5-positions (or the 4'- and the 5'-positions) can be considered as equivalent.

Illustrative of the substituents for the Y, A, B, R and R$^1$ moieties of the compounds of Formula I, $C_{1-6}$ alkyl preferably is methyl or ethyl but also includes the straight or branched manifestations having up to six carbon atoms such as propyl, isopropyl, n-, iso-, sec- or t-butyl, pentyl, hexyl and the like; $C_{1-6}$ alkoxy contains ethers paralleling the $C_{1-6}$ alkyl groups; halogeno preferably is chloro or bromo. When $(Y)_n$ is —S(O)$_m$R$^2$, preferably n is one and m is zero (i.e. —SR$^2$). R-substituted phenyl preferably is mono-substituted (in o-, m- or p- positions) but also includes di-substituted (i.e., 2,3-, 2,4-, 2,5-, 2,6-, 3,4- or 3,5-positions) or trisubstituted (i.e., 2,3,4-, 2,3,5-, 2,3,6- or 3,4,5-positions). When one of A or B is hydrogen, it is preferred that A be hydrogen.

The bi-imidazoles of the present invention are acidic and form salts with strong bases such as sodium hydroxide and potassium hydroxide.

The compounds of Formula I may be prepared by a number of syntheses wherein the process steps utilize procedures analogously known in the art. The syntheses which are generally applicable for the majority of the compounds of this invention conveniently utilize N-substituted protected imidazoles as starting materials.

One general pathway for the preparation of compounds of this invention is illustrated by the following Reaction Scheme A:

Reaction Scheme A

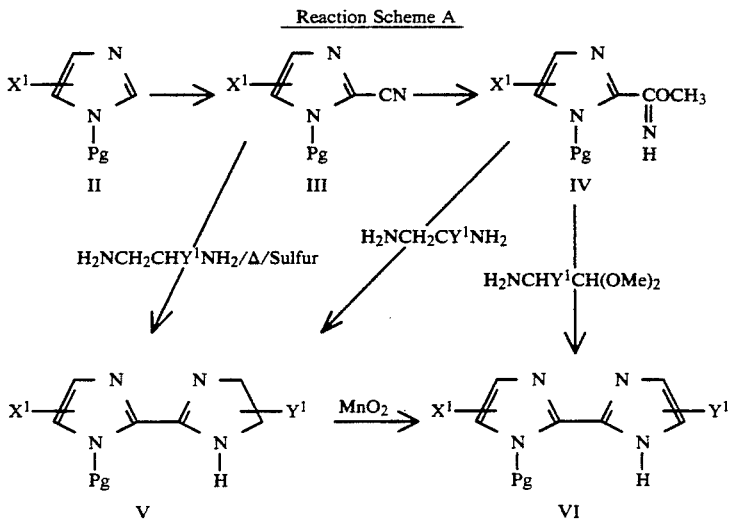

Reaction Scheme A

-continued

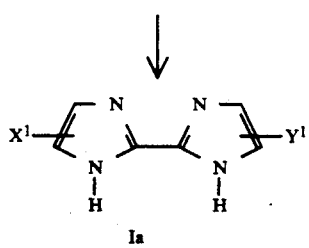

Ia wherein $X^1$ is hydrogen, cyano or a moiety convertible to cyano (e.g., $CONH_2$, $COOH$, etc.); $Y^1$ is hydrogen, alkyl, $CF_3$, pyridyl, phenyl, R-substituted phenyl, $COOR$ or $CONH_2$; Pg represents a protective group or, except for H, any group defined for B which is readily removed after the bi-imidazole is formed. The protective group can be exemplified by benzyl or substituted benzyl groups which can be readily removed by hydrogenation; by ethoxymethyl or 2-(trialkyl-silyl)ethoxymethyl which can be removed by hydrolysis. 2-(trimethylsilyl)ethoxymethyl (SEM) is a particularly preferred protecting group.

In essence, Reaction Scheme A is initiated by reacting an N-protected-$X^1$-substituted imidazole (II) with cyanogen chloride to form an in situ intermediate imidazolium ion which is treated with a base (e.g. triethylamine, metal carbonates, di-isopropylamine and the like) in a suitable solvent (e.g. DMF, acetonitrile, THF, etc.) to form an isolatable cyano derivative (III). The cyano derivatives (III) may be converted to their corresponding imidates via the Pinner reaction (i.e., treatment of an alcoholic solution of II with HCl gas, either with or without chloroform as a solvent). Alternatively the cyano derivatives (III) may be reacted with a $Y^1$-substituted ethylene diamine by heating the reactants, 80°–150° C. in the presence of sulfur to produce imidazoline imidazoles (V) which compounds may be converted to the desired bi-imidazoles (VI) by the introduction of a 4,5-double bond, preferably employing manganese dioxide as the oxidizing agent.

The imidates (IV) may also be converted to the corresponding imidazoline imidazoles (V) by reaction with an $Y^1$-substituted ethylene diamine (IIIa) and the reaction products similarly converted to the N-protected bi-imidazoles (VI) by introduction of the 4,5-double bond. Alternatively the imidate (IV) may be directly converted to the N-protected bi-imidazole (VI) by treatment of an Y'-substituted amino acetaldehyde dimethyl acetal (IIIG) with hydrochloric acid. Following these reactions, the N-protecting group(s) may be removed by standard procedures well known in the art.

Alternatively compounds of this invention may be prepared from the known compound 2,2'-bi-1H-imidazole (VII). The 2,2'-bi-1H-imidazole is converted to the novel N-protected 1,1'-[[2-(trimethylsilyl)ethoxy]methyl]-2,2'-bi-1H-imidazole derivative (VIII) by formation of the necessary di-anion with 2 equivalents of sodium hydride which di-anion is quenched with 2-(trimethylsilyl)ethoxymethyl chloride (i.e.,SEM-Cl) to form the desired di—SEM-protected inter mediate (VIII). This compound can then be used to prepare compounds of this invention according to the sequence shown in Reaction Scheme B.

Reaction Scheme B

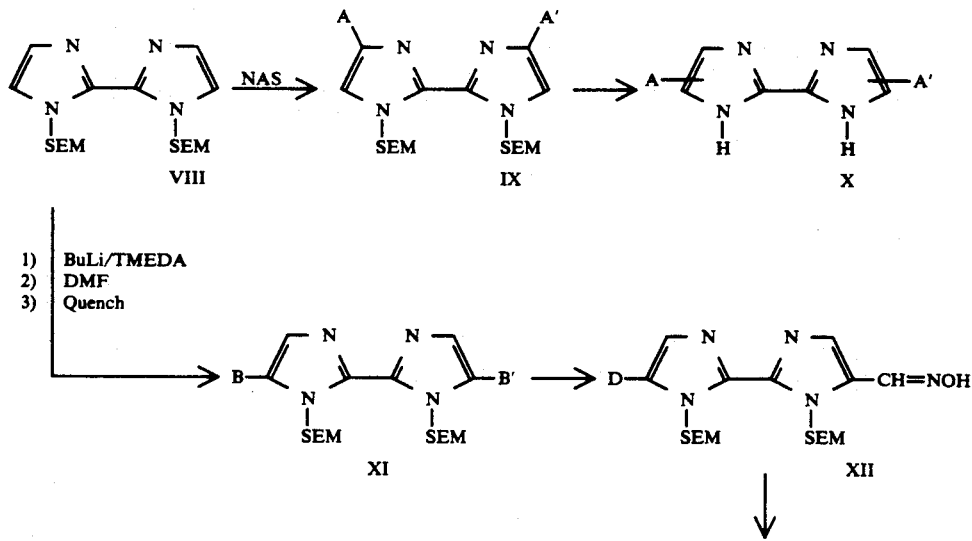

1) BuLi/TMEDA
2) DMF
3) Quench

-continued

Reaction Scheme B

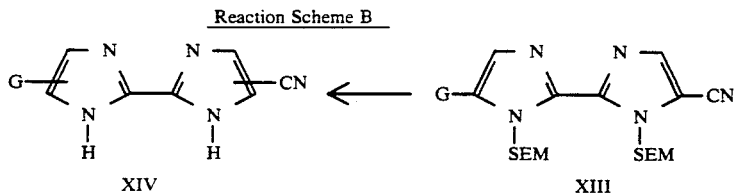

wherein
A is Cl or Br, A' is H, Cl, or Br,
B is H or CHO, B' is CHO,
D is H or —CH=NOH, G is H or CN, and
SEM is —CH$_2$OCH$_2$CH$_2$Si(Me)$_3$.

The di—SEM intermediate (VIII) is converted to either its mono- or di-aldehyde derivative (XI) by reaction with butyl lithium and tetramethylethylenediamine (TMEDA) in a suitable solvent (e.g. tetrahydrofuran) followed by treatment with dimethylformamide. The so-formed mono- and/or di-aldehyde derivatives (XI) may be converted to their corresponding nitriles, carboxyl, ester and amide derivatives by standard techniques well known in the art. For example, the aldehyde (XI) can be converted to the oxime (XII) which is then further converted to the protected carbonitrile (XIII) and the protecting groups are removed to give the desired product (XIV).

Alternatively the di-SEM-protected derivatives (VIII) may be halogenated by treatment with electrophiles N-bromo- or N-chlorosuccinimide using one or two equivalents in an inert solvent such as carbon tetrachloride. To obtain mixed halogen derivatives (wherein the halogen of A and A' of Formula IX are different) then sequential treatment with the N-bromosuccinimide and N-chlorosuccinimide reactants are necessary. Removal of the SEM-protecting groups may readily be achieved by acid hydrolysis (HCl/aqueous EtOH) or by treatment with tetra-butylammonium fluoride in THF to yield the desired products.

As indicated above, the 2,2'-bi-1H-imidazole starting material (VII) for Reaction Scheme B is already known in the literature but it can also be obtained by another convenient procedure wherein bis-methylimidate (i.e., dimethyl oximidate, CH$_3$O—C(=NH)—C(=NH)—OCH$_3$) is reacted with aminoacetaldehyde dimethyl acetal in ethanolic hydrogen chloride to yield a bis-amidine [i.e., N,N''-bis-(2-dimethoxyethyl)oxamidine]. The bis-amidine is converted to the desired 2,2'-bi-1H-imidazole by fusion ($\approx$170° C.) with a catalytic amount of p-toluenesulfonic acid. Alternatively the bis-amidine may be cyclized and aromatized to the desired 2,2'-bi-1H-imidazole by refluxing in 5 molar HCl. The necessary bis-methylimidate is obtained in good yield from cyanogen according to Weidinger, et al., Chem. Ber., 97, 1607 (1964).

Another procedure for the preparation of the present compounds, which can be considered as the preferred method for obtaining the present cyano compounds, involves the novel process depicted in Reaction Scheme C.

Reaction Scheme C

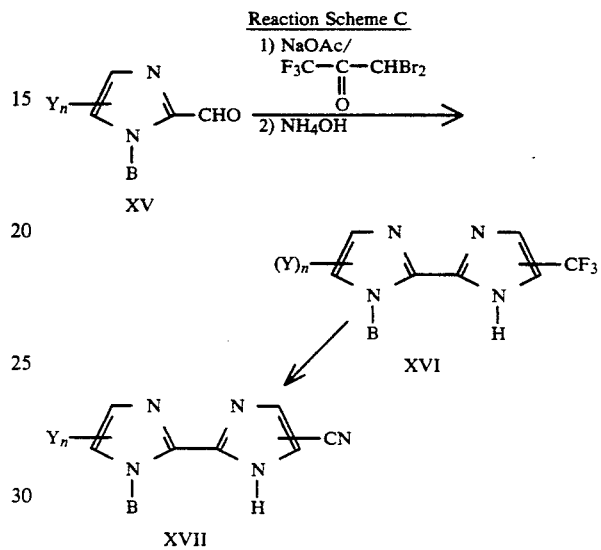

wherein Y$_n$ is as defined in Formula I, B is H, alkyl, vinyl, phenyl or benzyl.

In the preparation of the preferred compound XVII, the imidazole-2-carboxaldehyde XV is sequentially treated with trifluoromethylglyoxal (formed in situ from dibromotrifluoroacetone) and then ammonium hydroxide to provide the novel 4(5)-trifluoromethyl-2,2'-bi-imidazole (XVI), the trifluoromethyl moiety of which is readily converted to a cyano group by reaction with 5% ammonium hydroxide.

Having described the general methods of preparations for the compounds of this invention, the following specific examples are set forth to specifically illustrate these reactions. In no sense are they meant to be restrictive to the specific reactants, but are illustrative to a skilled artisan, taking into consideration that a skilled chemist would know the full range to which they may be applied when compounds of Formula I are sought to be made.

EXAMPLE 1

1-(Phenylmethyl)-1H-imidazole-2-carbonitrile

In a 50 ml 4-neck flask with stirring bar, nitrogen bubbler, gas inlet tube, thermometer, septum and acetonitrile (20 ml) was bubbled cyanogen chloride (3.1 g, 50 mmol) (ice bath was used to avoid mild heat of solution). The reaction was cooled in an ice bath and a solution of 1-benzylimidazole (3.16 g, 20 mmol) in acetonitrile (ca. 5 ml) was added via syringe. The colorless solution turned yellow-orange and within a few minutes a yellow-orange crystalline solid started to form. After 1 hour, the thick slurry was cooled to −20° C. and triethylamine (7 ml, 50 mmol) was added at such a rate to prevent the temperature from rising above 0° C. The mixture was stirred 1 hour while warming to room temperature, poured into saturated aq NaHCO$_3$ (100 ml) and extracted with ether (3×75 ml). The combined organic layers were dried (MgSO$_4$), evaporated and purified by Kugelrohr distillation. After a forerun of diethylcyanamide, the desired product was collected at 130° C. (0.4 mm) (3.05 g, 83%) as a colorless liquid which crystallized on standing, mp 51°-52° C. (cyclohexane).

EXAMPLE 2

1-[2-(Trimethylsilyl)ethoxymethyl]imidazole

A mixture of 2-(trimethylsilyl)ethoxymethyl chloride (11.6 g, 0.07 moles), imidazole (9.5 g, 0.014 moles) and dry toluene (100 ml) was stirred at room temperature for 18 hours, and the resulting imidazole hydrochloride was removed by filtration. The filtrate was concentrated to provide 13.4 g (97%) of crude product. Kugelrohr distillation at 94°-100° C. (0.2 mm) gave 8.92 g (65%) of the desired product as a colorless liquid.

EXAMPLE 3

2-Cyano-1-[2-(trimethylsilyl)ethoxymethyl]1H-imidazole

The reaction was run as in the preparation of Example 1 starting with 1.0 g (5 mmol) of the product of Example 2. After a forerun of diethylcyanamide, the desired product was collected at 110°-120° C. (0.4 mm) (0.74 g, 66%).

EXAMPLE 4

4-Methyl-1-(phenylmethyl)-1H-imidazole-2-carbonitrile (4A)

5-Methyl-1-(phenylmethyl)-1H-imidazole-2-carbonitrile (4B)

Under nitrogen, a 250 ml round-bottom flask was charged with 10 g (0.058 mol) 4(5)-methyl-1-(phenylmethyl)-1H-imidazole and 100 ml acetonitrile. The reaction was cooled to 5° C. and cyanogen chloride (5 g, 0.081 mol) sparged into the reaction. The reaction was worked up as in Example 1 and provided 13.1 g of crude product. Flash chromatography (500 ml Baker flash silica gel; 1:1 ethyl acetate/hexane) gave: 5.3 g of 4A as a colorless oil, bp 250° C. (0.1 mm) which slowly crystallized, mp 51.5°-52.5° C. (cyclohexane).

Continued elution gave 4B as a white solid, mp 112°-113° C. Also, 3.4 g of a mixture of 4A and 4B was obtained from the column. Overall yield of 4A and 4B was 84%.

EXAMPLE 5

1-Methyl-1H-imidazole-2-carbonitrile

The process of Example 1 was repeated using 1-methyl-1H-imidazole and the crude product obtained was purified by flash chromatography (ethyl acetate/hexane, 1:1) yielding a colorless oil in 82% yield; bp 70°-75° C. (0.4 mm) by Kugelrohr distillation.

EXAMPLE 6

5-Chloro-1-methyl-1H-imidazole-2-carbonitrile

Using the same type reaction as in Example 1, the desired product is subjected to Kugelrohr distillation of the oil resulting from the reaction work up at 45° C. (0.4 mm) to remove diethylcyanamide and at 60°-80° C. to give desired product as white crystals (product readily sublimes). Redistillation of the diethylcyanamide forerun gave additional compound. The combined crystals were triturated with hexane (warmed and recooled in an ice bath) and collected by filtration (2.5 g, 59%). Recrystallization of a portion of the crystals from cyclohexane gave shiny needles of analytically pure product, mp 87°-89° C.

EXAMPLE 7

4-Phenyl-1-(phenylmethyl)-1H-imidazole-2-carbonitrile

Under nitrogen, 2.0 g (0.0325 ml) cyanogen chloride was added to a 5° C. solution of 6.0 g (0.0256 mol) 4-phenyl-1-(phenylmethyl)-1H-imidazole in 100 ml acetonitrile/10 ml DMF. After 18 hour, the dark yellow reaction was warmed at 70° C. for 7 hours. After cooling, 4.5 ml (0.0325 mol) triethylamine was added and the reaction stirred overnight. The reaction was quenched with 300 ml saturated NaHCO$_3$ and extracted into ethyl acetate (3×150 ml). After drying and concentration, a tan oil was obtained. Flash chromatography (500 ml silica gel, EtOAc) gave 3.7 g recovered starting material and 2.26 g of the desired product (84% based on recovered starting material) mp 95°-96° C. (cyclohexane).

EXAMPLE 8

1-Phenylmethyl-4'(5')-methyl-2,2'-bi-1H-imidazole

A mixture of 1-benzyl-2-cyanoimidazole (5.49 g; 0.03 mole), sulfur (100 mg) and methoxyethanol (10 ml) was stirred under nitrogen and heated at 90° C. for 0.5 hour. 1,2-Diaminopropane (2.96 g, 0.04 mol) was added and the mixture heated at 100° C. for 2 hours. The mixture was allowed to cool to room temperature then partitioned between H$_2$O—CH$_2$Cl$_2$. The CH$_2$Cl$_2$ phased washed 2 times with H$_2$O and dried over MgSO$_4$. The CH$_2$Cl$_2$ solution was treated with 15 g activated MnO$_2$ at room temperature. The progress of the reaction was followed by TLC (30% MeOH in CH$_2$Cl$_2$). After 18 hours, an additional 5 g activated MnO$_2$ was added and the mixture stirred for 144 hours. The reaction was filtered through Celite and the pad was washed with CHCl$_3$. The filtrate and CHCl$_3$ wash were combined and evaporated in vacuo to yield an amber colored viscous oil. Flash chromatography on silica gel (10% CH$_3$OH—CH$_2$Cl$_2$) gave 3.1 g (43%) straw-colored solid; mp 120°-122° C.; MS (EI) m/z 238 (M+), 161 (M+-Ph).

EXAMPLE 9

2,2'-4(5)-Methylimidazoline-1H-imidazole

A mixture of 400 mg (4.3 mmol) 2-cyanoimidazole, 50 mg (1.6 mmol) sulfur and 10 ml 2-methoxyethanol was heated at 90° C. for ¼ hour then 0.7 ml (8.2 mmol) 1,2-diaminopropane was added and the mixture heated at 100° C. for 3 hours. The cooled mixture was treated with 15 ml benzene. A straw-color solid formed. After collection and drying, 0.4 g (63%) the desired product was obtained, mp 288°-289° C.

This product is oxidized to the desired corresponding 4(5)-methyl-2,2'-bi-1H-imidazole by following the oxidation procedure outlined in the second step of Example 8.

EXAMPLE 10

4(5)-Methyl-2,2'-bi-1H-imidazole

To a 500 ml flask containing a dry-ice condenser and submerged in an isopropanol dry-ice bath was placed 2.8 g (0.0118 mol) of the product of Example 8. To this was added approximately 250 ml liquid ammonia. The solution was stirred and tiny pieces of Na were added every 3 minutes until the blue color persisted. After 15 minutes, NH₄Cl (10 g) was added. The ammonia was allowed to evaporate over-night. The white solid residue was treated with 150 ml H₂O, filtered, washed with H₂O, dried, and washed with Et₂O. Analytically pure product of this example (1.5 9, 86%) was obtained as an off-white solid, mp 260° C.

EXAMPLE 11

1-Diethoxymethylimidazole

The procedure of Curtis and Brown was followed: Imidazole (204 g, 3.0M), triethyl orthoformate (1300 ml), and p-toluenesulfonic acid monohydrate (3.0 g) were placed in a 2-liter round bottom with a stirring bar and fitted with a Penn-State distillation head. The reaction was heated at reflux and ethanol removed by distillation. Heating was continued until the reaction temperature rose above 140° C. (ca. 2.5 hours). The reaction was cooled to room temperature and potassium carbonate was added to neutralize the acid catalyst. The desired product was isolated by distillation under vacuum, bp 105° C. (5 mm) after collecting a forerun below 105° C.

EXAMPLE 12

Imidazole-2-carboxaldehyde

In a dry 3 liter 3-neck round bottom flask with a football stirring bar, thermometer, 500 ml addition funnel equipped with a septum, and a nitrogen inlet valve was added 1-diethoxymethylimidazole (170 g, 1M) and anhydrous THF via a cannula. The solution was cooled to −40° C. and 2.6M n-butyl lithium in hexane (385 ml, 1M) was added dropwise at such a rate as to keep the inside temperature <−35° C. After complete addition, the reaction solution was kept at −40° C. for 30 minutes and anhydrous DMF (102 ml, 1.32M) was added in a slow stream keeping the reaction temperature at ca. −40° C. The reaction was warmed to room temperature and poured into 1N HCl (1 liter) in a 4-liter beaker. The two phase system was stirred and the upper hexane layer was evaporated with a stream of nitrogen. The pH of the remaining aqueous solution was ca. pH 9 and was acidified to pH 1 with concentrated HCl (ca. 200 ml). The light yellow-orange solution was stirred at room temperature for 15 minutes and was neutralized to pH 7 with 50% aqueous NaOH. A thick crystalline mass formed, which was cooled to 10° C. with an ice bath and the product was collected by filtration and washed with cold water (75.3 g, 78%); mp 198°-200° C. (dec). A second crop was obtained by evaporation of the filtrate to ca. 1 liter. The resulting precipitate (22 g) was recrystallized from water (200 ml) yielding golden crystals (10.4 g) mp 204°-205° C. (dec). Total yield: 85.7 g (89%).

EXAMPLE 13

4(5)-Trifluoromethyl-2,2'-bi-1H-imidazole 1,1-Dibromo-3,3,3-trifluoroacetone (252 g, 140 ml, 0.94M) was added to a solution of sodium acetate (138 g, 1.6M) in water (700 ml). The solution was heated on a steam bath for 30 minutes. To the cooled solution (ice bath) was added imidazole-2-carboxaldehyde (75 g, 0.78M), methanol (3 liter), followed by concentrated ammonium hydroxide (1 liter) (CAUTION: the NH₄OH addition is mildly exothermic). A homogenous reaction mixture was obtained and after 1 hour product began to crystallize. After stirring overnight at room temperature the desired product was collected by filtration and dried (77.7 g, 49.3%). This material was sufficiently pure to carry on to the next step. Recrystallization of a small sample from xylene provided an analytical sample, mp 239°-241° C.

EXAMPLE 14

4(5)-Cyano-2,2'-bi-1H-imidazole

A sample of 2.5 g (0.0124 moles) the product of Example 13 was mixed with 200 ml 5% aqueous ammonium hydroxide and warmed to 60° C. After 1 hour, TLC (ethyl acetate) and HPLC (particle 10 ODS Cl8 column) (acetonitrile:0.04M sodium dihydrogen phosphate:0.04M sodium hydrogen phosphate, 1:2.5:2.5) 1.5 ml/minute) showed that the reaction was completed and no starting material remained. The cooled reaction was carefully neutralized with glacial acetic acid to give 1.83 g (93%) of product as a light-pink solid. Recrystallization (2-methoxyethanol) gave pure product, mp >260° C. In a similar manner there are prepared 1'-methyl-4(5)-cyano-2,2'-bi-1H-imidazole; 1'-methyl-5'-chloro-4(5)-cyano-2,2'-bi-1H-imidazole; 1'-ethyl-4(5)-cyano-2,2'-bi-1H-imidazole; 1'-vinyl-4(5)-cyano-2,2'-bi-1H-imidazole; 1'-phenyl-4(5)-cyano-2,2'-bi-1H-imidazole; 1'-benzyl-4(5)-cyano-2,2'-bi-1H-imidazole, as well as the corresponding 5'-chloro or 5'-bromo of the latter 4-named compounds.

EXAMPLE 15

N-Ethylimidazole-2-carboxaldehyde

Under nitrogen, a solution of 15.1 g (0.157 moles) N-ethylimidazole and 150 ml tetrahydrofuran was cooled to −40° C. Sixty-three ml 2.6M n-butyllithium in hexane (0.164 moles) was added via syringe. After fifteen minutes, 12.8 ml N,N-dimethylformamide was added and the reaction was allowed to warm to room temperature. After 18 hours the reaction was quenched with 5N hydrochloric acid. After stirring 15 minutes, the tetrahydrofuran was removed under reduced pressure. The remaining aqueous solution was basified with potassium carbonate solution and the product extracted into ethyl acetate (3×150 ml). After drying (anhydrous sodium sulfate) and concentration, 18.15 g (93.2%) of product was obtained as a pale tan oil, bp 90° C. at 12 mm.

EXAMPLE 16

4'(5')-(Trifluoromethyl)-5-chloro-1-methyl-2,2'-bi-1H-imidazole

A mixture of 7.6 g (0.028 moles) 1,1-dibromo-3,3,3-tri-fluoroacetone, 2.5 g (0.3 moles) sodium acetate and 15 ml water was heated on a steam bath for ½ hour, cooled, and the cooled solution was added to 3.4 g (0.0235 moles) 5-chloro-1-methylimidazole-2-carboxaldehyde in 100 ml methanol. Finally, 25 ml concentrated ammonium hydroxide was added slowly. After stirring for 5 hours at room temperature, the reaction was concentrated and then extracted with ethyl acetate (2×75 ml). After drying (anhydrous sodium sulfate) and concentration, 5.3 g gummy-tan solid was obtained. Recrystallization (toluene) gave 2.16 g (36.7%) light tan crystals, mp 217°-219° C. In a similar manner there are prepared 4'(5')-(trifluoromethyl)-5-chloro-1-ethyl-2,2'-bi-1H-imidazole; 4'(5')-(trifluoromethyl)-5-chloro-1-vinyl-2,2'-bi-1H-imidazole; 4'(5')-(trifluoromethyl)-5- chloro-1-phenyl-2,2'-bi-1H-imidazole; 4'(5')-(trifluoromethyl)-5-chloro-1-benzyl-2,2'-bi-1H-imidazole, the corresponding-5-bromo analogs and the corresponding 5-des-chloro derivatives, as well as those Y-substituted compounds of Formula 1 wherein $Y_n$ is as defined therein.

EXAMPLE 17

1-Methyl-4-cyano-2,2'-bi-1H-imidazole (a) and

1-Methyl-5-cyano-2,2'-bi-1H-imidazole (b)

Under nitrogen, a mixture of 0.92 g (0.023 moles) 60% sodium hydride (washed with hexane to remove the mineral oil) and 150 ml N, N-dimethylformamide was charged with 3.4 g (0.021 moles) 4(5)-cyano-2,2'-bi-1H-imidazole. The reaction was warmed at 50° C. for 15 minutes to insure complete anion formation, cooled to room temperature and 1.33 ml (0.021 moles) iodomethane added. After 18 hours, the reaction was diluted with water and extracted with ethyl acetate (3×200 ml). After drying (anhydrous sodium sulfate) and concentration 4.6 g oily solid was obtained. The two isomers were separated by flash chromatography (hexane:ethyl acetate, 1:1) to give 1.5 g (40.5%) of (a) and 0.3 g (8.1%) (b).

(a) mp 237°–239° C. (toluene/isopropanol);
(b) mp 238°–239° C. (toluene/isopropanol);

EXAMPLE 18

1,1'-Bis[[2-(trimethylsilyl)ethoxy]methyl]-2,2'-bi-1Himidazole

Under a blanket of nitrogen, 8.2 g (0.172 moles) 50% sodium hydride was washed with hexane. The flask was charged with 250 ml dry N,N-dimethylformamide and 11.5 g (0.086 moles) 2,2'-bi-1H-imidazole was added in small portions. After stirring at room temperature for 1½ hours 30.8 g (0.185 moles) 2-(trimethylsilyl)ethoxymethyl chloride (SEM-Cl) was added dropwise. The reaction exothermed slightly. The reaction was stirred for 1 hour then quenched with water and extracted into ethyl acetate (3×200 ml). The combined organic layers were shaken with water (2×300 ml), dried (anhydrous sodium sulfate) and concentrated to give 33.4 g tan oil. The product was purified by preparative HPLC (ethyl acetate) to give 26.9 g (79.2%) desired product as a light tan oil. A small portion was distilled. bp 260° C. at 0.2 mm.

EXAMPLE 19

4'(5')-Trifluoromethyl-5-chloro-1-methyl-2,2'-bi-1H-imidazole

A mixture of 7.6 g (0.028 moles) 1,1-dibromo-3,3,3-tri-fluoroacetone, 2.5 g (0.3 moles) sodium acetate and 15 ml water was heated on a steam bath for 1–2 hour. This cooled solution was added to 3.4 g (0.0235 moles) 5-chloro-1-methylimidazole-2-carboxaldehyde in 100 ml methanol. Finally, 25 ml concentrated ammonium hydroxide was added slowly. After stirring for 5 hours the reaction was concentrated and then extracted with ethyl acetate (2×75 ml). After drying (anhydrous sodium sulfate) and concentration, 5.3 g gummy-tan solid was obtained. Recrystallization (toluene) gave 2.16 g (36.7%) light tan crystals, mp 217°–219° C. NMR (dimethyl sulfoxide-d6) δ3.15–3.80 (br s, 1H), 4.05 (s, 3H), 7.19 (s, 1H), 7.86 (s, H); ms (70 eV, electron impact) m/e 250 (molecular ion), 231 (M+-F), 215 (M³⁰-Cl).

Anal. Calcd. for $C_8H_6F_3ClN_4$; C, 38.34; H, 2.41; N, 22.36. Found: C, 38.43; H, 2.44; N, 22.17.

EXAMPLE 20

4-(Trifluoromethyl)-1,1'-bis[[2-(trimethylsilyl)ethoxy]-methyl]-2,2'bi-1H-imidazole To 14.4 g (0.3 mol) 50% NaH (washed 3 times with hexane to remove the mineral oil) and 300 ml DMF, was slowly added 26.3 g (0.13 mol) 4-(trifluoromethyl)-2,2'-bi-1H-imidazole as a solid. The reaction was stirred for 2 hours at room temperature and then heated at 40° C. for 2 hours. Next, 50 g (0.3 mol) SEM-Cl was added dropwise. After 1 hour, the reaction was quenched with water (1 liter) and the product extracted into EtOAc (3×150 ml). After drying (NaSO₄) and concentration, 51.2 g crude product was obtained. Purification by preparative HPLC (37% EtOAc/63% hexane) gave 16.7 g (28%) desired product as a tan oil; ¹H NMR (CDCl₃) δ-0.14 (s, 18), 0.61-1.0 (m, 4), 3.25-3.70 (m, 4), 5.76 (s, 2), 5.81 (s, 2), 0.61-1.0 (m, 4), 3.25-3.70 (m, 4), 5.76 (s, 2), 5.81 (s, 2), 6.91-7.06 (m, 2), 7.36 (s br, 1); MS (CI/CH₄) m/z 463 (MH+).

EXAMPLE 21

4-Bromo-4'-(trifluoromethyl)-1,1'-bis[[(trimethylsilyl)-ethoxy]methyl]-2,2'-bi-1H-imidazole A mixture of 11.1 g (0.024 mol) of the compound of Example 20 and 250 ml CCl₄ was treated with 4.89 g (0.028 mol) N-bromosuccinimide. The reaction was refluxed for 3 hours, cooled, filtered, and concentrated to give 12.5 g crude product. Flash chromatography (5% EtOAc/hexane) gave 5.56 g (43%) of desired product as a tan oil; ¹H NMR (CDCl₃) δ-0.14 (s, 18), 0.65-1.00 (m, 4), 3.25-3.60 (m, 4), 5.70 (s, 2), 5.72 (s, 2), 7.00 (s, 1), 7.31 (s br, 1); MS (CI/CH₄) m/z 541 (MH+).

EXAMPLE 22

4(5)-Bromo-4'(5')-(trifluoromethyl)-2,2'-bi-1H-imidazole

A mixture of 4.9 g of the compound of Example 21, 40 ml 40% HBr, 40 ml water and 200 ml EtOH was warmed at 80° C. for 3 hours. The EtOH was removed under vacuum and the resulting slurry was neutralized with aqueous K₂CO₃. The white solid (2.42g, 96%) was collected; mp >260° C.; ¹H NMR (DMSO-d₆) δ7.45 (s, 1), 7.95 (s br, 1); MS (EI at 70 eV) m/z 280 (M³⁰-F), 201 (M³⁰-Br).

Anal. Calcd for $C_7H_4BrF_3N_4$: C, 29.92; H, 1.43; N, 19.94. Found: C, 29.80; H, 1.53; N, 19.75.

EXAMPLE 23

4(5)-Bromo-4'(5')-cyano-2,2'-bi-1H-imidazole

A sample of 1.52 g (5.4 mmol) of the compound of Example 22 was added to 250 ml 5% NH₄OH. Over a period of 4 days the solid slowly dissolved. The reaction was neutralized with HOAc and 0.55 g (43%) of the desired product was collected as a white solid; mp>260° C. (EtOAc); IR (nujol) 2240 cm⁻¹; ¹H NMR (DMSO-d6) 7.35 (s, 1), 8.15 (s, 1); MS (EI at 70 eV) m/z 237 (M+), 158 (M³⁰-Br), 131 (M+-Br-HCN).

Anal. Calcd for $C_7H_4BrN_4$: C, 35.33; H, 1.69; N, 29.42. Found: C, 35.37; H, 1.93; N, 29.76.

By utilizing the techniques of the foregoing specific examples and the generic procedures set forth in Reaction A, B and C there may be produced such additional representative compounds of formula I as follows:

4(5),4'(5')-di-cyano-2,2'-bi-1H-imidazole;
4(5)-methyl-4'(5')-cyano-2,2'-bi-1H-imidazole;
4(5)-trifluoromethyl-4'(5')-cyano-2,2'-bi-1H-imidazole;
4(5)-(2-pyridyl)-4'(5')-cyano-2,2'-bi-1H-imidazole, its 3- or 4-pyridyl isomers;
4(5-carboxy-4'(5')-cyano-2,2'-bi-1H-imidazole;
4(5)-carbamyl-4'(5')-cyano-2,2-bi-1H-imidazole;
4(5)-methylthio-4'(5')-cyano-2,2-bi-1H-imidazole and the sulfinyl and sulfonyl analogs;
4(5)phenyl-4'(5')cyano-2,2-bi-1H-imidazole and its alkyl, halogeno, nitro, amino, alkoxy, $CF_3$, or $-S(O)_m$ alkyl (m is zero, one or two) substituted phenyl analogs.

As stated above this invention relates to the use of certain 2,2'-bi-1H-imidazoles of Formula I to enhance myocardial contractile force. Thus the compounds are useful as cardiotonics in the treatment of heart failure. The compounds also lower high blood pressure and thus are useful as antihypertensive agents.

Heart failure is that physiological condition resulting from the inability of the ventricular myocardium to maintain adequate blood flow to the peripheral body tissues and includes congestive heart failure, backward and forward heart failure, right ventricular and left ventricular heart failure, and high-output and low-output heart failure. Heart failure can be caused by myocardial ischemia, myocardial infarction, excessive alcohol usage, pulmonary embolism, infection, anemia, arrhythmias, and systemic hypertension. Symptoms include tachycardia, fatigue with exertion, dyspnea, orthopnea and pulmonary edema.

Treatment involves either removal or correction of the underlying cause or involves control of the heart failure state. Management or control can be accomplished by increasing cardiac output or by decreasing cardiac workload. While workload can be reduced by reduction of physical activities and physical and emotional rest, increasing cardiac output has traditionally involved digitalis therapy. Digitalis stimulates contractile force of the heart which increases cardiac output and improves ventricular emptying. In this way digitalis therapy normalizes venous pressure and reduces peripheral vasoconstriction, circulatory congestion and organ hypoperfusion.

Unfortunately, optimal doses of digitalis vary with the patient's age, size and condition and the therapeutic to toxic ratio is quite narrow. In most patients the lethal dose is only about five to ten times the minimal effective dose with toxic effects becoming apparent at only 1.5 to 2.0 times the effective dose. For these reasons, dose must be carefully tailored to suit the individual and frequent clinical examination and electrocardiogram is necessary to detect early signs of digitalis intoxication. Despite this care digitalis intoxication is reported in up to one-fifth of hospitalized patients undergoing therapy.

The need for less toxic cardiotonic agents is readily apparent. Applicants have discovered certain 2,2-bi-1Himidazole which possess potent cardiotonic activity and by comparison to digitalis have few toxic effects.

The utility of the compounds of formula I as cardiotonics may be determined by administering the test compound (0.1-100 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. Heart failure is induced by administering sodium pentobarbital (20 to 40 mg/kg) followed by a continuous infusion of sodium pentabarbital at 0.25-2 mg/kg/minute. Alternatively, propranalol hydrochloride (4 mg/kg) can be used to induce heart failure followed by a continuous infusion of 0.18 mg/kg/minute of propranolol hydrochloride to the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compound may be administered alone or in the form of pharmaceutical preparations to the patient being treated either topically, orally or parenterally, that is, intravenously or intramuscularly. The amount of compound administered will vary with the patient, the severity of the cardiac failure and the mode of administration.

For topical, oral or parenteral administration the cardiotonically effective amount of compound and the amount required to enhance myocardial contractile force is from about 0.1 mg/kg of patients body weight per day up to about 400 mg/kg of patient body weight per day and preferably from about 0.3 mg/kg of patient body weight per day up to 120 mg/kg of patient body weight per day.

For oral administration a unit dosage may contain, for example, from 5 to 700 mg of the active ingredient, preferably about 15 to 235 mg of the active ingredient. For parenteral administration a unit dosage may contain, for example, from 5 to 700 mg of the active ingredient, administration of the compounds may be desired and will vary with the condition of the patient and the mode of administration.

Some of the compounds of this invention also exhibit anti-hypertensive effects, particularly 4(5)-cyano-2,2'-bi-1H-imidazole. The antihypertensive aspect of the compounds of this invention may readily be determined by standard laboratory procedures. For example, spontaneously hypertensive rats (SHR) weighing 325-375 g (24-28 weeks old) are used for testing. Continuous direct recording of arterial blood pressure and heart rate is determined in freely moving conscious and anesthetized rats from a cannulated left carotid artery. The test compound is administered (orally (po) or intravenously (IV)) to SHR's. Results of in vivo activity on blood pressure changes in SHR's for 4(5)-cyano 2,2'-bi-1H-imidazole showed an ED-20% at 4.6 mg/kg with I.V. administration and an ED-20% at 10.5 with oral administration. Further oral administration of this compound produced dose related mean arterial pressure (MAP) a moderate increase in heart rate (HR); these changes being of long duration (e.g. at 30 mg/kg a $-36\%$ MAP for 17 hours and a plus 23% HR for 17 hours).

As used herein, the term "patient" is taken to mean warm blooded mammalians such as sheep, horses, bovines, pigs, dogs, cats, and humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general Formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compounds in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

As is true for all classes of compounds found to be useful as chemotherapeutic agents, certain subgeneric groups and certain specific compounds exhibit superior end-use biological profiles than others of the same class. It is preferred that both A and B be hydrogen, with either group being alkyl, aryl, or aralkyl being next preferred. The preferred Y substituents are methyl, halogen (chloro or bromo), cyano, trifluoromethyl, or aryl. Preferred specific compounds are:

4(5), 4'(5')-dicyano-2,2'-bi-1H-imidazole, mp >250° C.;
(5)-cyano-4'(5')-trifluoromethyl-2,2'-bi-1H-imidazole, mp >250° C.;
4(5)-cyano-4'(5')-phenyl-2,2'-bi-1H-imidazole, mp >260° C.;
4(5)-cyano-2,2'-bi-1H-imidazole, mp >260° C.;
4(5)-cyano-4'(5')-(4-trifluoromethylphenyl)-2,2'-bi-1H-imidazole, mp >250° C.;
4(5)-cyano-4'(5')-(4-methoxyphenyl)-2,2'-bi-1H-imidazole, mp >280° C.;
4(5)-cyano-1'-methyl-2,2'-bi-1H-imidazole, mp >260° C.;
4,5-dibromo-4'(5')-cyano-2,2'-bi-1H-imidazole, mp >260° C.;
1-methyl-4-cyano-2,2'-bi-1H-imidazole, mp 237°-239° C.;
1-methyl-5-cyano-2,2'-bi-1H-imidazole, mp 238°-239° C.;
5'-chloro-1'-methyl-4(5)cyano-2,2'-bi-1H-imidazole, mp 259°-261° C.;
1-ethyl-5-cyano-2,2'-bi-1H-imidazole, mp 117°-118° C.;
4'(5')-chloro-4(5)-cyano-2,2'-bi-1H-imidazole, mp >250° C.;
4'(5')-methyl-4(5)-cyano-2,2'-bi-1H-imidazole, mp >260° C.;
1'-(phenylmethyl)-4(5)-cyano-2,2'-bi-1H-imidazole, mp 239°-241° C.;
1'-ethyl-4(5)-cyano-2,2'-bi-1H-imidazole, mp 215°-216° C.;
1-(phenylmethyl)-4-cyano-2,2'-bi-1H-imidazole, mp 189°-190° C.;
1'-phenyl-4(5)-cyano-2,2'-bi-1H-imidazole, mp 222°-225° C.;
1'-ethenyl-4(5)-cyano-2,2'-bi-1H-imidazole, mp >260° C.

What is claimed is:

1. A compound of the formula

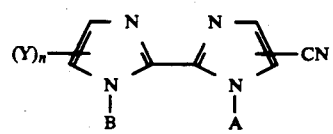

the tautomers thereof, or a pharmaceutically acceptable salt thereof, wherein

N is 1 or 2; when n is 1, Y is hydrogen, halogen, $C_{1-6}$ alkyl, $C_{1-6}$ alkoxy, $CF_3$, 2-, 3-, or 4-pyridyl, $COOR^1$, $CONH_2$, $-S(O)_mR^2$ phenyl and R-substituted phenyl with R being hydrogen, $C_{1-6}$ alkyl, halogeno, nitro, amino, $C_{1-6}$ alkoxy, $CF_3$ or $-S(O)_mR^2$; and when n is 2, Y is hydrogen, halogen or $C_{1-6}$ alkyl; $R^1$ is hydrogen or $C_{1-6}$ alkyl; $R^2$ is $C_{1-6}$ alkyl; m is zero, one or two;

A is hydrogen or $C_{1-6}$ alkyl:

B is hydrogen or methyl, ethyl, vinyl, phenyl or benzyl with the proviso that at least one of A or B is hydrogen.

2. A compound according claim 1 which has the formula

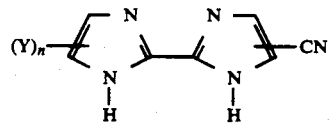

the tautomers thereof, or a pharmaceutically acceptable salt thereof, wherein n is 1 or 2; when n is 1, Y is hydrogen, halogen, $C_{1-6}$ alkyl, $C_{1-6}$ alkoxy, $CF_3$, 2-, 3-, or 4-pyridyl, $COOR^1$, $CONH_2$, $-S(O)_mR^2$ phenyl and R-substituted phenyl with R being hydrogen, $C_{1-6}$ alkyl, halogeno, nitro, amino, $C_{1-6}$ alkoxy, $CF_3$ or $-S(O)_mR^2$; and when n is 2, Y is hydrogen, halogen or $C_{1-6}$ alkyl; $R^1$ is hydrogen or $C_{1-6}$ alkyl; R is $C_{1-6}$ alkyl; m is zero, one or two.

3. A compound according to claim 1 which is 4,5-dibromo-4'(5')-cyano-2,2'-bi-1H-imidazole.

4. A compound according claim 1 which has the formula

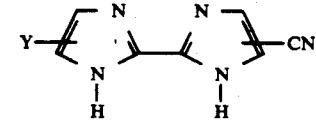

the tautomers thereof, or a pharmaceutically acceptable salt thereof, wherein

Y is hydrogen, halogen, $C_{1-6}$ alkyl, $C_{1-6}$ alkoxy, $CF_3$, 2-, 3-, or 4-pyridyl, $COOR^1$, $CONH_2$, $-S(O)_mR^2$ phenyl and R-substituted phenyl with R being hydrogen, $C_{1-6}$ alkyl, halogeno, nitro, amino, $C_{1-6}$ alkoxy, $CF_3$ or $-S(O)_mR^2$; $R^1$ is hydrogen or $C_{1-6}$ alkyl; $R^2$ is $C_{1-6}$ alkyl; m is zero, one or two.

5. A compound according to claim 1 which is 4(5)-cyano-2,2'-bi-1H-imidazole.

6. A compound according to claim 1 which is 4(5),4'(5')-dicyano-2,2'-bi-1H-imidazole.

7. A compound according to claim 1 which is 4(5)-cyano-4'(5')-trifluoromethyl-2,2'-bi-1H-imidazole.

8. A compound according to claim 1 which is 4(5)-cyano-4'(5')-phenyl-2,2'-bi-1H-imidazole.

9. A compound according to claim 1 which is 4(5)-cyano-4'(5')-(4-trifluoromethylphenyl)-2,2'-bi-1H-imidazole.

10. A compound according to claim 1 which is 4(5)-cyano-4'(5')-(4-methoxyphenyl)-2,2'-bi-1H-imidazole.

11. A compound according to claim 1 which has the formula

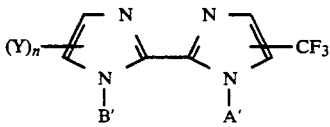

the tautomers thereof, or a pharmaceutically acceptable salt thereof, wherein

B is hydrogen or methyl, ethyl, vinyl, phenyl or benzyl.

12. A compound according to claim 1 which is 4'(5')-methyl-4(5)-cyano-2,2'-bi-1H-imidazole.

13. A method of treating a patient suffering from heart failure which comprises administering a cardiotonically effective amount of a compound of claim 1.

14. A compound of the formula the tautomers thereof wherein Y and n are as defined in claim 1; A' is hydrogen, $C_{1-6}$ alkyl Or 2-(trimethylsilyl)-ethoxymethyl; and B' is hydrogen, methyl, ethyl, vinyl, phenyl, benzyl or 2-(trimethylsilyl)ethoxymethyl.

* * * * *